(12) United States Patent
Wu et al.

(10) Patent No.: US 9,390,888 B2
(45) Date of Patent: Jul. 12, 2016

(54) APPARATUS AND METHOD OF APPLYING SMALL-ANGLE ELECTRON SCATTERING TO CHARACTERIZE NANOSTRUCTURES ON OPAQUE SUBSTRATE

(71) Applicant: Industrial Technology Research Institute, Hsinchu (TW)

(72) Inventors: Wen-Li Wu, Hsinchu (TW); Yun-San Chien, Kaohsiung (TW); Wei-En Fu, Taoyuan (TW); Yen-Song Chen, Taipei (TW); Hsin-Chia Ho, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/720,122

(22) Filed: May 22, 2015

(65) Prior Publication Data
US 2015/0340201 A1    Nov. 26, 2015

Related U.S. Application Data

(60) Provisional application No. 62/002,537, filed on May 23, 2014.

(51) Int. Cl.
| | |
|---|---|
| *H01J 37/00* | (2006.01) |
| *H01J 37/29* | (2006.01) |
| *H01J 37/06* | (2006.01) |
| *H01J 37/145* | (2006.01) |
| *H01J 37/04* | (2006.01) |
| *H01J 37/295* | (2006.01) |
| *G01N 23/20* | (2006.01) |

(52) U.S. Cl.
CPC .......... *H01J 37/29* (2013.01); *G01N 23/20058* (2013.01); *H01J 37/04* (2013.01); *H01J 37/06* (2013.01); *H01J 37/145* (2013.01); *H01J 37/295* (2013.01); *H01J 2237/0492* (2013.01); *H01J 2237/255* (2013.01)

(58) Field of Classification Search
USPC ........................................................ 250/307
See application file for complete search history.

(56) References Cited

U.S. PATENT DOCUMENTS

| | | | | |
|---|---|---|---|---|
| 5,093,573 | A * | 3/1992 | Mikoshiba | ....... G01N 23/20058 250/307 |
| 5,536,940 | A * | 7/1996 | Alvis | ..................... H01J 37/05 250/305 |
| 5,866,905 | A * | 2/1999 | Kakibayashi | ........ G01N 23/046 250/311 |
| 7,504,625 | B2 * | 3/2009 | Yamazaki | ............... H01J 37/04 250/306 |

(Continued)

OTHER PUBLICATIONS

Koyama; et. al "Small angle electron diffraction and deflection", AIP Advances 2, 012195 (2012), pp. 2-8.*

(Continued)

*Primary Examiner* — Phillip A Johnston

(57) ABSTRACT

An apparatus and methods for small-angle electron beam scattering measurements in a reflection or a backscattering mode are provided. The apparatus includes an electron source, electron collimation optics before a sample, electron projection optics after the sample, a sample stage capable of holding the sample, and a electron detector module. The electrons emitted from the source are collimated and positioned to impinge nanostructures on the sample. The signals resulting from the interactions between the impinging electrons and the nanostructures are further magnified by the electron projection optics to reach a sufficient angular resolution before recorded by the electron detector module.

21 Claims, 5 Drawing Sheets

(56) References Cited

U.S. PATENT DOCUMENTS

| | | | |
|---|---|---|---|
| 7,920,676 B2 | 4/2011 | Yun et al. | |
| 8,247,769 B2 | 8/2012 | Zewail | |
| 8,692,204 B2 | 4/2014 | Kojima et al. | |
| 8,921,783 B2 * | 12/2014 | Billinge | G01N 23/20058 250/306 |
| 2014/0161233 A1 | 6/2014 | Ollinger et al. | |

OTHER PUBLICATIONS

Ayahiko Ichimiya et al., "Reflection High Energy Electron Diffraction," Frontmatter, 2004, pp. 1-366, Cambridge University Press, US.

T. Koyama et al., "Small Angle Electron Diffraction and Deflection," AIP Advances, Feb. 2012, 8 pages, vol. 2, No. 1, AIP Publishing, US.

* cited by examiner

APPARATUS AND METHOD OF APPLYING SMALL-ANGLE ELECTRON SCATTERING TO CHARACTERIZE NANOSTRUCTURES ON OPAQUE SUBSTRATE

CROSS REFERENCE TO RELATED APPLICATIONS

This application claims the benefit of U.S. Provisional Application No. 62/002,537, filed on May 23, 2014, hereby incorporated by reference in its entirety.

BACKGROUND

1. Field of the Invention

The present invention relates generally to the characterization of nanostructures on opaque or thick substrates. More particularly, the present invention relates to electron beam metrology in both reflection and backscattering modes applicable to the large sample sizes encountered in today's semiconductor fabrication environments.

2. Description of the Related Art

Reflection high-energy electron diffraction (RHEED) is a powerful analytical tool widely used for characterizing thin film growth in molecular beam epitaxy. It provides great sensitivity in measuring the atomic arrangements, which are in sub-nanometers, of a surface layer by monitoring the electron diffraction patterns; it also has been applied to measuring surface morphology by monitoring total reflection intensity [Ayahiko Ichimiya and Philip I. Cohen, Reflection High-Energy Electron Diffraction Cambridge University Press, 2004 (ISBN 0 521 45373 9)].

In a typical operation of RHEED, its incident electron beam often encompasses an energy range from about 8 to 20 kilo electron volt (KeV), though it can be employed at electron energies as high as 50 KeV to 100 KeV. To characterize atomic arrangements, the incident electron beam impinges the sample surface at a low glancing angle of a few degrees, and a diffraction beam spread over a range of few degrees. There are no lenses or electron optics between the sample and the detector since the angular range of the pertinent signals exists from a few degrees to tens of degrees. At a reasonable distance, the resolution of today's detector used in RHEED is sufficient to resolve the diffraction pattern in the reflected electron beam. However, it is not feasible to use the conventional RHEED technique to resolve the small-angle scattering signals to reach a sufficient angular resolution in characterizing structures on a nanometer scale.

Throughout this disclosure, the term "diffraction" is used in its classical definition adopted in X-ray crystallography; a probing beam, which can be X-ray, electron or neutron, after impinging on a crystalline material, will be diffracted if the condition specified by Bragg's law is fulfilled. Based on Bragg's law, the scattering or the diffraction beam occurs in wide angles from a few degrees to tens of degrees as the wavelength of the probing beam is comparable or larger than the characteristic length scale of the target material. In X-ray applications this phenomenon is dubbed as wide angle X-ray scattering, this name indicates that diffraction is also a scattering event caused by crystalline lattices and the diffraction angle is between a few degrees to tens of degree; hence the term "wide angle" in contrast to the term "small angle" appearing in the title of this application. Conversely, as the wavelength of the probing beam is less than the characteristic length of the target material, the scattering occurs in small angles of a few degrees or less.

Measurements similar to RHEED have also been conducted in transmission electron microscopy (TEM) and it has been coined as reflection electron microscopy (REM). This was first developed by Honjo and Yagi's group in exploring the atomic re-organization on silicon single crystal surface. [K. Yagi, K. Takayanagi, and G. Honjo, (1982), In Crystals, Growth, Properties and Applications vol. 7 Springer-Verlag, Berlin-Heidelberg, pp. 48-74] Using a high-energy electron beam to characterize structures of nanometer scale or at high angular resolutions has been conducted in conventional TEM; however, all the measurements have been carried out by monitoring the transmitted electron beam i.e. in transmission mode instead of the reflection and/or backscattering modes.

Transmission small-angle X-ray scattering (tSAXS) [T. Hu, R. L. Jones, W. L. Wu, E. K. Lin, Q. H. Lin, D. Keane, S. Weigand and J. Quintana, J. Appl. Phys. 96, (2004) pp. 1983-1987.] and grazing incident small-angle X-ray scattering (GISAXS) [J. Wernecke, M. Krumrey, A. Hoell, R. J. Kline, H. K. Liu and W. L. Wu, J. Applied Crystallography 47(6) (2014) pp. 1912-20] are two other relevant techniques using X-ray to probe nanostructures on flat substrates. The former one chooses X-ray with sufficient energy to penetrate the substrate, e.g. for silicon wafers commonly used in Today's semiconductor fabrication the incident X-ray used was typical above 13 KeV for a sufficient transmission power over ~0.7 mm silicon wafer. Synchrotron X-ray sources have often been used for tSAXS measurement and this approach is not amendable to the use in testing laboratories or fabrication lines in semiconductor industries.

Current laboratory X-ray sources can provide appropriate energy level for tSAXS as well as a reasonably small beam size, about 50 μm, on samples; however, the measurement time is often in the range of hours or even longer due to the limited X-ray flux available from today's laboratory X-ray sources. To overcome this deficiency of low X-ray flux, GISAXS has been considered as a viable alternative. By lowering the incident angle from 90 degrees, as in the case of tSAXS, to a few degrees, the footprint, hence, the sampling area of GISAXS can be increased significantly. This, in turn, leads to an increase in scattering signal over tSAXS for a given incident X-ray flux. However, a large footprint of the incident beam on samples is impractical for many applications, e.g. the test pattern in semiconductor fabrication is often limited to 100 μm×100 μm or less.

The feature size in the nanostructures produced by today's semiconductor industries approaches 10 nanometers (nm) and beyond, which corresponds to an angle range of a few hundredths to a few thousandth of a degree when electron beams at kilo electron volts (KeV) are used as the probe. This minuscule angular range necessitates a novel high resolution apparatus operated in either a reflection or backscattering modes—the aim of this patent application.

SUMMARY

One objective of this invention is located on characterizing structures existed on an opaque or thick substrate, i.e., not amendable for any electron measurements of transmission type. Another objective of this invention is aimed to measure structures significantly larger than the atomic scale by one to several orders of magnitude. In this scales, the angular range within which the relevant scattering signals exist is ten times or even smaller than that of RHEED/REM.

To achieve these and other advantages and in accordance with the objective of the invention, as embodied and broadly described herein, the present invention is configured as follows.

According to some embodiments, a novel apparatus for small-angle electron scattering in reflection/backscattering modes is provided. This apparatus includes an electron source, a number of electron collimation optics before the sample, a number of electron projection optics after the sample, a sample stage capable of aligning and holding a sample of 40 cm diameter or larger, and a detector module. The electrons emitted from the source are collimated and positioned to impinge on a small target nano-patterned area on an opaque substrate. The signals resulting from the interactions between the impinging electrons and the nanostructures are further magnified by the electron projection optics to reach a sufficient angular resolution before recorded by the detector module.

According to some embodiments, a novel method of small-angle electron scattering in reflection mode is provided. An electron source is configured to emit electrons. These electrons are reflected/scattered by a target nano-patterned area on an opaque substrate; these reflected/scattered electrons are further magnified by a set of electron projection optics to reach a sufficient angular resolution before recorded by an electron detector module.

According to some embodiments, a novel method for small-angle electron scattering in backscattering mode is provided. An electron source is configured to emit electrons. After impinging the sample these electrons are backscattered which are further scattered by the target nanostructure located on an opaque substrate, these backscattered then scattered electrons are further magnified by a set of electron projection optics to gain a sufficient angular resolution before recorded by an electron detector module.

The difference between the present invention and the conventional RHEED/REM includes the apparatus and methods of the above embodiments being capable of measuring or characterizing nano-structure formed on an opaque or thick substrate. Specifically, in both RHEED and REM their target is the surface atomic arrangement in sub-nanometer; whereas the present invention is aimed to measure structures significantly larger than the atomic scale by one to several orders of magnitude. This results in a major difference in the angular range within which the relevant scattering signals exist between the present invention and RHEED/REM; the angular range of interests to the present invention is ten times or even smaller than that of RHEED/REM.

The present invention also address the aforementioned difficulties encountered by X-ray based methods even it also adopts a low grazing incident geometry. This is because of the following characteristics of electron beam. First of all, an electron beam size of a few nanometers can now be achieved routinely, for example, the size of today's electron beams used in TEM approaches a few nanometers. Even operated at a low grazing incident angle its footprint is expected to be much less than a few micrometers instead of millimeters as for GISAXS. Thus, measurement of a desired area (e.g., 100 µm×100 µm or less) of a large substrate (e.g., 400 mm in diameter) can be realized by using electron beam. In addition, the issue of low beam flux is compensated for by the fact that the scattering cross section between target sample and electron beam is about 4 orders of magnitude greater that between matters and X-ray, i.e. the electron beam scattering signal is intrinsically about $10^4$ times stronger than that from X-ray. This intrinsic property of electrons alleviates the difficulty encountered by X-rays in lacking of beam intensity. The above discussion of the sampling area or the footprint area of the probing electron beam also reveals a major difference between SAES and the conventional scanning electron microscopy. At any given time the SAES signal comes from a collection of the features at nanoscale while the signal of the latter comes from an area less than individual feature size.

BRIEF DESCRIPTION OF THE DRAWINGS

For a more complete understanding of the embodiments, and the advantages thereof, reference is now made to the following descriptions taken in conjunction with the accompanying drawings.

DESCRIPTION OF THE ILLUSTRATIVE EMBODIMENTS

In the following descriptions, an apparatus and method of applying small-angle electron scattering to characterize nanostructures on opaque substrate of the present invention will be explained with reference to embodiments thereof. It should be appreciated that these embodiments are not intended to limit the present invention to any specific environment, applications or particular implementations described in these embodiments. Therefore, the description of these embodiments is only for the purpose of illustration rather than to limit the present invention. Furthermore, the attached drawings may be drawn in a slightly simplified or exaggerated way for ease of understanding; the numbers, shapes and dimensional scales of elements depicted may not be exactly the same as those in practical implementations and are not intended to limit the present invention.

In this patent invention a novel electron beam (e-beam) apparatus and methods capable of characterizing nanostructures on a large opaque substrate with a minimum or no sample preparation is proposed. The apparatus and methods of the present invention are discussed in two categories; one for scattering signals collected in a reflection mode and the other for signals collected in a backscattering mode.

1. Small-Angle Electron Scattering in Reflection Mode

Figure 1:
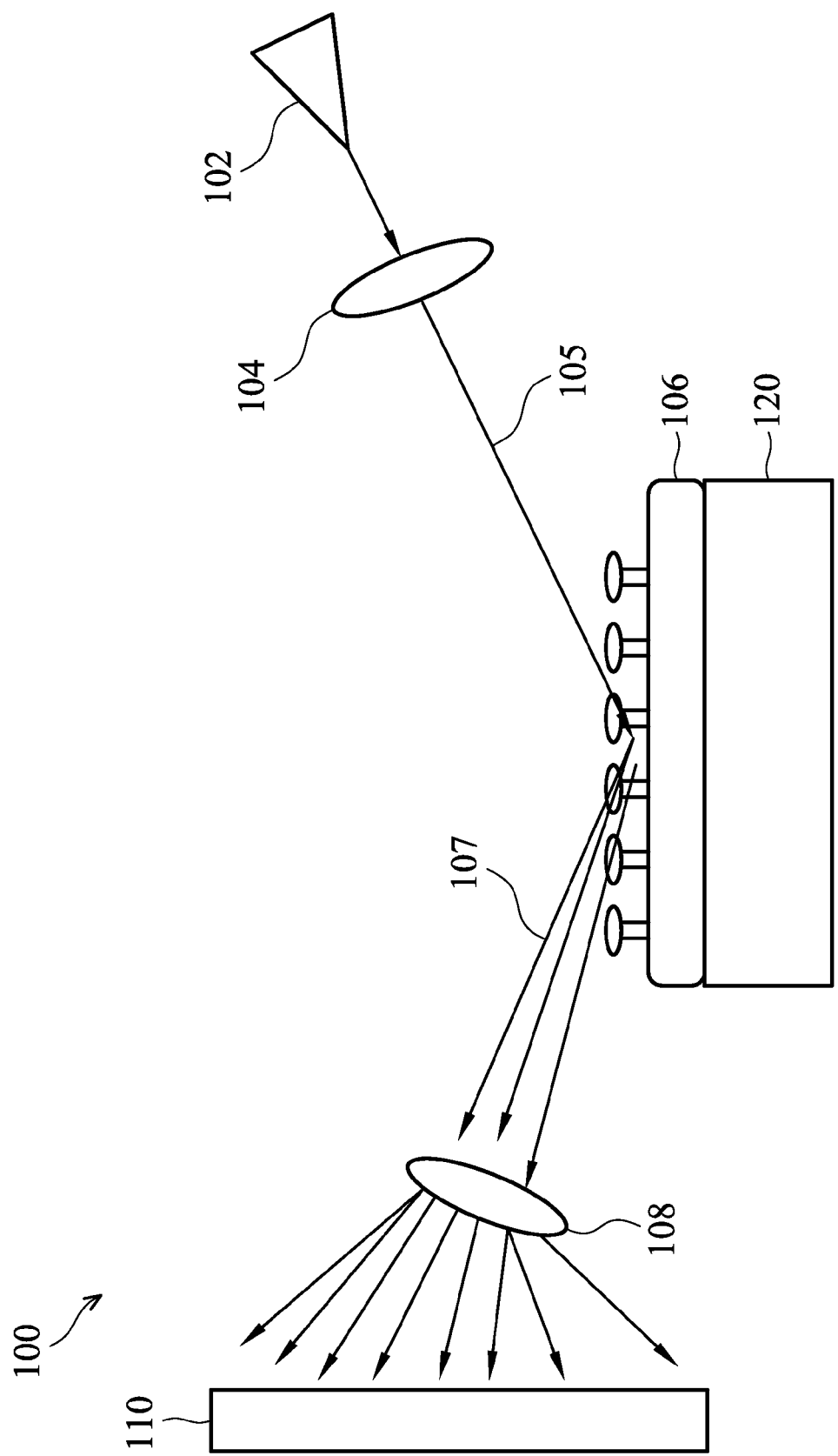
FIG. 1 is a schematic diagram of an electron beam small-angle scattering measurement in a reflection mode, in accordance with some embodiments.

FIG. 1 is a schematic diagram of a reflection small-angle electron beam scattering apparatus 100 (referred to RSAES apparatus 100 hereinafter) in accordance with some embodiments of the invention. The RSAES apparatus 100 is used to characterizing nanometer-scale features existed in a sample 106. In the rest of this invention the term RSAES will be used as a synonym of the high angular resolution measurements for acquiring relevant scattering data from structures at nanometers instead of the atomic scale of sub-nanometer. In accordance with some embodiments of the invention, the various components of the RSAES apparatus 100 may be implemented as follows.

The RSAES apparatus 100 includes an electron source 102, a number of electron collimation optics 104, a number of electron projection optics 108, an electron beam detector module 110, and a sample stage 120, in accordance with some embodiments. The elements of the RSAES apparatus 100 can be added to or omitted, and the disclosure should not be limited by the embodiments. It should be appreciated that the components of the electron collimation optics 104 and the electron projection optics 108 are shown as a single lens only for clarity.

The electron source 102 is implemented to supply a high brilliance electron beam. In some embodiments, the electron source 102 is a cold field emission electron guns (CFEG). The CFEG is used to produce an electron beam that is smaller in diameter, more coherent and with a current density or brightness that is up to three orders of magnitude greater than what can be achieved with the thermionic emitters. The CFEG emits small and high brilliance electrons while kept at room temperature in a strong electric field. Since the energy spread of the emitted electrons 102 from the CFEG is narrower (about 0.4 eV) than all other types, the CFEG is preferred for high coherence measurements. The CFEG is also a low energy spread technique, and therefore can be used in energy resolved RSAES. The electron source 102 may continuously produce an electron beam over an extended period of time, such as weeks or longer, with minimal disruptive maintenance efforts.

Alternatively, the electron source 102 is a thermionic type electron gun such as tungsten or lanthanum hexaboride (LaB6)-tipped filaments. The thermionic type electron gun provides a higher emission current than that of CFEG and may be used to characterize a sample in which the coherence effects are not needed.

In some embodiments, the electron source 102 is implemented to provide electron flux with energy with low KeV, from a few KeV to tens of KeV. The electron beam with KeV energy possesses an unsurpassed intrinsic spatial resolution due to its wavelength in the range of picometers (pm). In all embodiments, the housing of the electron source 102 needs to be in vacuum. The extent of the vacuum depends on the type of electron emitters used. For example, the electron scattering measurements operate at a vacuum of $10^{-6}$ Torr, a LaB6 source operates at $10^{-7}$ Torr, and a CFEG emitter operates at $10^{-9}$ Torr or better in the gun region.

As shown in FIG. 1, the electron collimation optics 104 are positioned after the electron source 102 and before the sample 106. The electron collimation optics 104 are configured to receive and to direct the electron beam from the electron source 102 to the sample 106. In some embodiments, the tilt angle or position of the electron collimation optics 104 is arranged corresponding to that of the electron source 102, so that the electron source 102 and the electron collimation optics 104 are configured and operated in coordination to enable a grazing incident angle of the electron beam from less than one degree to near 90 degrees.

The electron collimation optics 104 may also enable the incident electron beam 105 to be precisely controlled in its size, beam cross sectional shape, its position, and its incident angle. The electron collimation optics 104 may be used to collimate the electron beam from the electron source 102 and to generate an incident electron beam 105 which is going to be impinged on the sample 106. The beam convergence angle of the incident electron beam 105 can be divergent, convergent or parallel.

In some embodiments, the electron collimation optics 104 include a set of components selected from a group consisting of electromagnetic lenses, magnetic lenses, electrostatic lenses, apertures, reflective mirrors, deflectors (deflection lenses) and prisms. The specific details of the arrangement of lenses depend on the size and the shape of the target area on the sample 106.

The electron projection optics 108 are positioned after the sample stage 120 and before the electron detector module 110. The electron projection optics 108 are configured to receive scattered electrons from the sample 106 and direct the scattered electrons to the electron detector module 110. By changing the tilt angle, either electronically or physically or both, of the electron projection optics 108 the scattered/reflected electrons from the sample 106 at low grazing exit angle of less than one degree to a high grazing exit angle near 90 degrees can be received, processed and recorded.

In some embodiments, the electron projection optics 108 include a set of components selected from a group consisting of electromagnetic lenses, magnetic lenses, electrostatic lenses, apertures, reflective mirrors, deflection lenses and prisms. The specific details of the arrangement of the electron collimation optics 108 depend on the scattering signals to be collected.

In some embodiments, the electron projection optics 108 include a glazing angle magnifying component positioned immediately adjacent to the sample stage 120. The glazing angle magnifying component can be a prism or a reflective mirror or a combination of both. The exit grazing angle of the scattering electron from the sample 106 is magnified by the glazing angle magnifying component to a high grazing exit angle. With the glazing angle magnifying component, the other components of the electron projection optics 108 can be positioned farther away from the sample 106 than the glazing angle magnifying component, which provides more flexibility in the layout of the electron projection optics 108. However, it should be appreciated that many variations and modifications can be made to embodiments of the disclosure.

In some embodiments, the electron projection optics 108 also include an energy filter. The energy filter is used to filter out electrons that are not in the preselected energy ranges. In operation, the energy filter may generate an electric or magnetic field, the electrons in the preselected energy range are transmitted through while the remaining electrons are blocked or deflected. In some embodiments, the energy filter is integrated within the electron detector module 110 instead of the electron projection optics 108.

The electron detector module 110 is configured to detect electron signals emerging from the sample 106 at one or multiple angles. In some embodiments, the tilt angle or position of the electron detector module 110 is arranged corresponding to that of the electron projection optics 108, so that the electron projection optics and the electron detector module are configured and operated to receive electrons at low grazing exit angle of less than one degree to a high grazing exit angle near 90 degrees.

In some embodiments, the electron detector module 110 includes a detector, such as including a scintillator and CCD, to receive the scattering electrons from the sample 106 and convert that electron current into detection signals. Alternate signals such as secondary electrons, backscattered electrons, Auger electrons, and fluorescent X-ray produced from the interactions between electron beam 105 and the sample 106 may also be simultaneously collected in the region near the sample by one or more detectors.

In some embodiments, the RSAES apparatus 100 also includes a controller (not shown in figures). A controller may control one or more of the electron collimation optics 104 and the sample stage 120 to selectively scan the electron beam probe in the sampling areas in a continuous or a step scanning mode.

The sample stage 120 is configured for holding, positioning, moving, and otherwise manipulating the sample 106. In some embodiments, the sample stage 120 is configured to accommodate a sample of up to 40 cm in diameter or more. In some embodiments, the sample stage 120 is capable of adjusting the height of the sample 106. In some embodiments, the sample stage 120 is also designed and configured to be operable for translational motion. The precision of stage translation in all three directions (two lateral directions plus the height) needs to be a small fraction of the target area size from tens of nanometers to tens of micrometers.

In some embodiments, the sample stage 120 is further designed operably to tilt or dynamically change the tilt angle relative to an electron beam 105 from the electron collimation optics 104. The angular precision of the stage alignment is preferably to be in the range of one milli-radian (mrad) or less in all three Euler angles. As a result, the sample stage 120 is able to translate a given sampling area to the incident beam 105 and also to align the target with respect to the electron beam 105 in all three Euler angles.

In some embodiments, the sample 106 includes a semiconductor wafer having various device elements. Examples of device elements that are formed in the sample 106 include transistors (e.g., metal oxide semiconductor field effect transistors (MOSFET), complementary metal oxide semiconductor (CMOS) transistors, bipolar junction transistors (BJT), high-voltage transistors, high-frequency transistors, p-channel and/or n-channel field-effect transistors (PFETs/NFETs), etc.), diodes, and/or other applicable elements. In some embodiments, the surface of the sample 106 includes some nanometer-scale features. For example, the sample 106 includes a number of metal lines, pillars, holes, gates and other 3D structures each having a dimension in nanometers.

In some embodiments, the sample 106 includes an opaque substrate. The term "opaque" not only indicates the substrate being opaque to visible light but indicates that the substrate is opaque to electron beams. In some embodiments, the substrate is made of materials with a thickness that is impenetrable by electrons in KeV ranges (e.g., electron with few KeV to tens of KeV).

Figure 2:
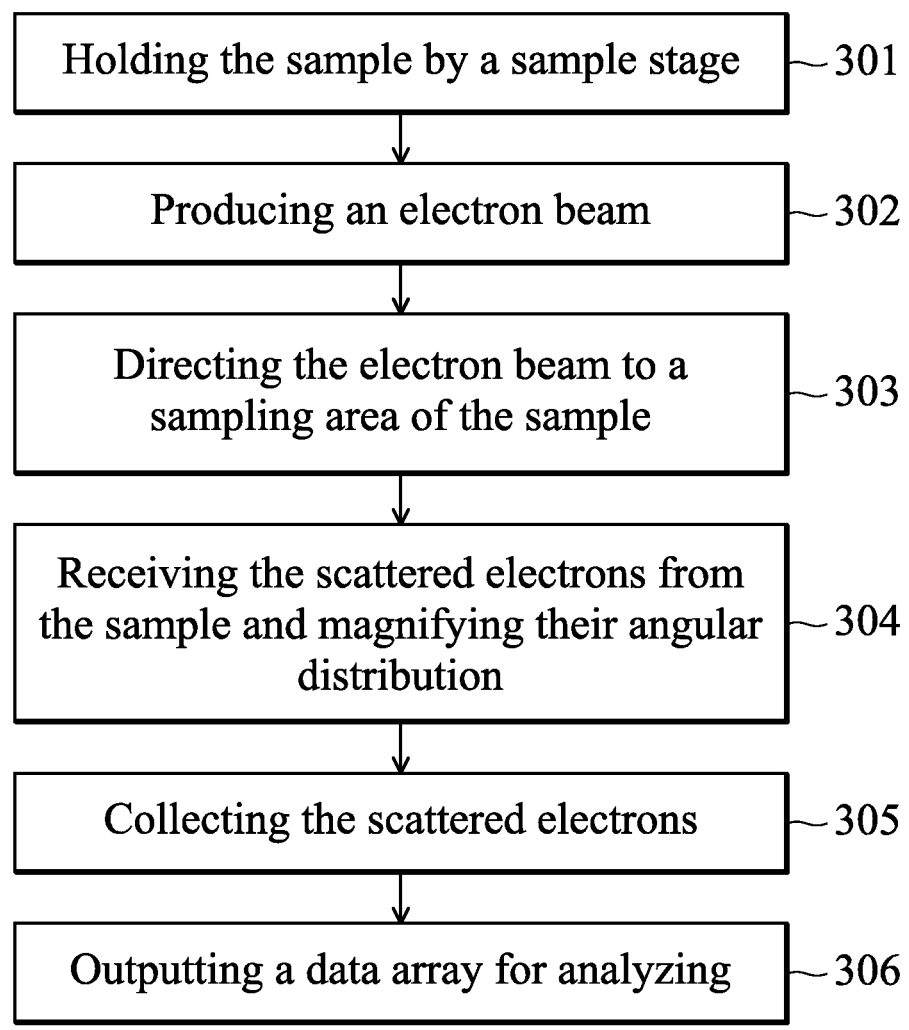
FIG. 2 a flow chart of methods for characterizing surface features in nanometers from a sample, in accordance with some embodiments.

FIG. 2 is a flow chart illustrating a method 300 for characterizing surface features in nanometers from a sample in either a reflection mode, or a backscattering mode or both, in accordance with some embodiments. For illustration, the flow chart will be described along with the schematic diagrams shown in FIG. 1. Some of the stages described can be replaced or eliminated for different embodiments.

The method begins with an operation 301, in which a sample (such as sample 106) is held by a sample stage 120. Before the positioning of the sample 106 on the sample stage 120, various processing steps are used to fabricate integrated circuits on the sample. The semiconductor feature size is in nanometers.

The method continues with an operation 302, in which an electron beam 105 is produced by an electron source (such as electron source 102). In some embodiments, electron flux with energy with low KeV is generated by the electron source 102. For example, the wavelength of electron beam 105 is 12.3 pm at 10 KeV; 5 pm at 50 KeV and 3.70 pm at 100 KeV,
note that these values are much smaller than the 154 pm X-ray wavelength commonly used in the laboratory. In general, the acceleration voltage of the electron beam 105 is in a range of about 20 KeV or less for operation in reflective mode, and the acceleration voltage of the probing electron beam 105 can be higher than 20 KeV for operation in backscattering mode.

The reason for the use of low KeV electrons as the probe is described below. When a collimated electron beam impinges on a nano-scale structure at a small glancing angle (usually less than a few degrees), the scattered/reflected electron beam from the sample surface carries information about the surface structures. Since the wavelength of the electron beam is in pm and depends on the energy of the incident e-beam, the relevant scattering signal occurs in an angular range of $10^{-2}$ radians or less. Its exact value also depends on the energy of the incident electron beam. Taking 10 nm diameter nanoparticles on top of a flat substrate as the target sample, the scattering intensity from the incident beam falls rapidly as the grazing detection angle, measured in the reflection plane, goes beyond $3 \times 10^{-5}$ radians or $1.7 \times 10^{-3}$ degrees when a 100 KeV e-beam is used. This small angular range expands somewhat as low KeV electrons are used as the probing e-beam; this is desirable. Another reason for the use of low KeV electrons as the probe is to enhance the reflected electron beam intensity which, by itself, can act as a source of scattering to provide more signals for characterizing the target nanostructures.

The method continues with an operation 303, in which the electron beam 105 is directed to a sampling area of the sample 106 by electron collimation optics (such as electron collimation optics 104). In some embodiments, in order to project the electron beam 105 to the interested sampling area of the sample 106, the position where the electron beam 105 illuminates is adjusted by the electron collimation optics 104. For example, a scan coil of the electron collimation optics 104 is used to deflect the electron beam 105 in the X and Y axes so that it scans in a raster fashion over the sample 106. In some embodiments, the electron collimation optics 104 and the sample stage 120 are operated in coordination to direct the electron beam 105 to different areas on the sample 106 in scanning, non-scanning, step scanning, or continuous scanning modes.

In some embodiments, a combination of the electron collimation optics 104 and the sample stage 120 is used to control the incident angle of the electron beam 105 on the sample 106. For example, during the period of the scanning process performed by the electron collimation optics 104, the sample stage 120 adjusts the tilt angle of the sample 106 in all three Euler angles in mrad. In some embodiments, the electron source and the electron collimation optics are configured and operated in coordination to enable a grazing incident angle of the electron beam 105 from less than one degree to near 90 degrees.

In some embodiments, in order to characterize features in the sampling area efficiently, the whole region in the sampling area is illuminated by the electron beam 105. As a result, the size and the beam cross sectional shape of the electron beam 105 are also adjusted by the electron collimation optics 104. For example, an electromagnetic lens of the electron collimation optics 104 is used to control the size of the electron beam. The electromagnetic lens includes a coil of wire through which electrical current flows. By controlling the current applied thereto, the diameter and the cross section shape of the electron beam is varied. The size of the electron beam on the sample 106 is several micrometers to tens of micrometers in its linear dimension. Additionally, the control of the size and the cross section shape of the electron beam on the sample can be realized by the combination of the electron source 102 and the electron collimation optics 104.

As shown in FIG. 1, after the projection of the electron beam 105, a scattered/reflected electron beam 107 is generated from the sample 106. The scattered/reflected electron beam 107 may include components from the scattering of the incident electron beam 105 by the nanostructure, the scattering of the reflected beam by the nanostructure, a combination of both and even other complex multiple scattering events. The scattered/reflected electron beam 107 emanates from the sample at low exit grazing angle of a few degrees or less due to the fact that both the reflectivity and the scattering of e-beam fall off rapidly with the exit grazing angle.

The method continues with an operation 304, in which the scattered/reflected electron beam 107 at low grazing exit angle which can be as low as less than one degree from the sample 106 is conditioned and magnified by the electron projection optics 108.

To condition the scattered/reflected electron beam 107, the scattered electron beam 107 may be deflected to a high grazing exit angle by a glazing angle magnifying member to allow the installation of electro-optical components close to the sample 106 up to 40 cm diameter or even larger. Alternatively or additionally, the scattered electron beam 107 may be filtered by an energy filter. For example, elastic and inelastic contributions in the scattered electron beam 107 are separated, so that information which is useful to identifying the origin of the scattering events can be recorded. As a result, the scattering contrast and the ability to detect sample composition can be enhanced.

To magnify the scattered/reflected electron beam 107, the angular distribution of the scattered electron beam 107 may be expanded to achieve a high resolution scattering pattern. The scattered/reflected electron beam 107 is magnified by all the necessary processes to achieve an effective sample-to-detector distance ($L_{eff}$, i.e., a value of effective distance from the sample to the electron detector module) up to 100 meters. This corresponds to an angular resolution from about $10^{-4}$ rad to about $10^{-5}$ rad.

In some embodiments, the electron collimation optics 104 and the electron projection optics 108 are configured and operated in coordination to magnify the angular resolution. For example, the focus length of the electron collimation optics 104 is adjusted to provide a focal point before the sample 106. The electron projection optics 108 are adjusted to place the mirror image of this focal point, in this case the surface of the opaque substrate acts as the mirror, in the object plane of 108 and to focus also to magnify this mirror image of the focal point onto the detector module 110. In some embodiments, the focal point of the electron collimation optics can be placed beyond the sample 106, again, the functions of the projection optics 108 are to focus and to magnify the mirror image of this focal point from 104 onto the detector module 110. Integrating electron optics system, including electro-optics both before and after the sample, to enable long $L_{eff}$ or high angular resolution is a major difference between the present invention and a conventional RHEED.

The method continues with an operation 305, in which the scattered/reflected electron beam 107 is collected by an electron detector module (such as electron detector module 110) and analyzed. It should be appreciated that in the present invention the probing electrons are initiated at the electron source 102, however, useful scattering information carried in the electrons reaching the detector module is not limited to what directly scattered/reflected by the incoming electron beam from the electron source alone. The reflected electrons, the backscattered electrons and even the diffracted electrons can interfere with the nanostructures and can carry information about the nanostructures as long as the system resolution is adequate. As a result, within the context of this invention, the scattered/reflected electrons comprise those from the scattering of the incident beam, the scattering of the reflected beam, the reflection of the scattering beam, their combinations, and other multiple scattering-reflection events.

In addition, other electron types such as secondary electrons and Auger electrons can also be valuable to provide complimentary information about the nanostructure, e.g. the shadow of the sample from secondary electrons can provide information about the grazing incident angle of the direct electron beam. The case of the scattering of nanostructures by backscattered electrons will be discussed later. In some embodiments, in order to enable the selection of the energy range of the electron received by the electron detector module 110, an energy filtering member is utilized before or in the electron detector module 110.

The diffracted electrons from different crystalline parts of the sample can interfere among themselves to provide useful information. The embodiment given in FIG. 1 only shows the case of scattering of the direct incident electron beam for clarity, in certain sense this can be considered as a special case of scattering of the diffracted electrons. The direct beam is basically a diffracted electrons of zero order. To collect the scattered signals from diffracted electrons one needs to align the sample and the incident beam to have the specific diffracted electrons aligned with the optical axis of electron projection optics 108. In other words, any one of the diffracted beams can be used as a direct incident beam to gather complimentary scattering information when the nanostructures of interests located in various positions in the sampling area have identical crystalline structure and orientation. The above condition is commonly met in semiconductor fabrications; for example, in etched patterns on silicon, GaAs and other single crystal wafers and nanostructures made of epitaxial layers grown on a single crystal wafer.

It is advantageous to choose diffraction beams with significant intensity for the abovementioned scattering measurements. By fine-tuning both the grazing incident angle and the azimuthal angle of the sample, a surface wave resonance condition can be fulfilled [S. Miyake, and K. Hayakawa, Acta Crystallogr. A26, (1970) 60-70] to significantly enhance the intensity of the diffraction beam of interests. The scattering signal resulted from this specific diffraction beam is expected to be enhanced concurrently.

The method continues with an operation 306, in which a data array is output for analyzing. In some embodiments, a two dimensional data array with the angular information encoded in the position of the array is output to a controller for analysis. Alternatively and additionally, a data array which has been resolved by an energy filter in each data point of the array is output.

In some embodiments, the electron beam 105 will result in a charge accumulation on sample 106. As more and more electrons are accumulated the scattering events begin to be adversely dominated by the charging effect. To address this problem, an excessive sample charging is therefore controlled via various techniques. The techniques may include decreasing accelerating voltage; coating the non-conducting samples with a thin conductive film; applying biasing voltage to the sample surface; using low vacuum; and mounting a conductive bridge connecting the top of the sample surface to the stage. The voltage distributions from sample charging across various nanostructures made of different materials in the sampling area can be appraised to provide information about their material types and their local electric conductivity. Even without any sample charging, the material type in various parts of the nanostructures can also be appraised via RSAES based on the material dependence of the mean internal potential of electron.

To illustrate the feasibility of RSAES in reflection mode, a TEM with the capability of tilting both the incident beam and the sample stage has been used despite the fact that a TEM is not even close to be the apparatus described in the present invention. A TEM was used simply because it was readily available. With a custom-made sample holder and a tailor cut sample of about 1 mm in size a RSAES type demonstration run was conducted with a JEM2100 TEM. RHEED apparatus just does not have sufficient angular resolution for this type of work, hence, it was not chosen. In TEM communities a "high dispersive (HD)" mode has been widely adopted to achieve transmission scattering patterns with a high angular resolution [T. Koyama, K. Takayanagi, Y. Togawa, S. Mori, and K. Harada, AIP ADVANCES 2, 012195 (2012)] and it is a built-in operation mode in certain commercial TEM, e.g. JEOL 2000 series. In HD mode, the effective sample-to-detector distance ($L_{\mathit{eff}}$) can be adjusted between two to $10^2$ meters despite the fact that the physical distance between the sample and the detector is merely a meter or less for a conventional TEM.

In a conventional HD protocol of TEM operation, the condenser lens adjacent to the sample is over-focused, its cross-over point located above the sample can be considered as a virtual scattering spot of the sample. The distance between this virtual scattering spot and the sample can be much greater than the focal length of the objective lens, and hence it provides the basis of achieving high $L_{\mathit{eff}}$ values up to $10^2$ m. With a $L_{\mathit{eff}}$ of $10^2$ m a scattering angle of $1.7\times10^{-3}$ degrees turns into a distance of ~3000 μm on a detector, this is readily discernible given that the spatial resolution of a typical detector is near 100 μm or better. However, this HD protocol, while providing high resolution, suffers a significant loss in the intensity. This loss in intensity reflects the fact that the sample is illuminated by a point-like source located a far distance away from the sample, i.e. the sample receives a divergent beam emanating from a distant point source. A different protocol has been applied in this invention to overcome this deficiency of loss in intensity while keeping its high resolution; the condenser lens adjacent to the sample is highly under focused such that the cross-over exists at a distance below the sample. This cross-over also acts as a virtual scattering spot while the sample is illuminated by a convergent electron beam. This scheme is dubbed convergent beam high dispersive, or CHD. It is noteworthy that the term convergent beam does not imply that the converging point is located in the sample as is the case for traditional converging beam TEM operations. It is also noteworthy that in both the HD and the CHD modes, the objective lens of the TEM is turned off.

Figure 3:
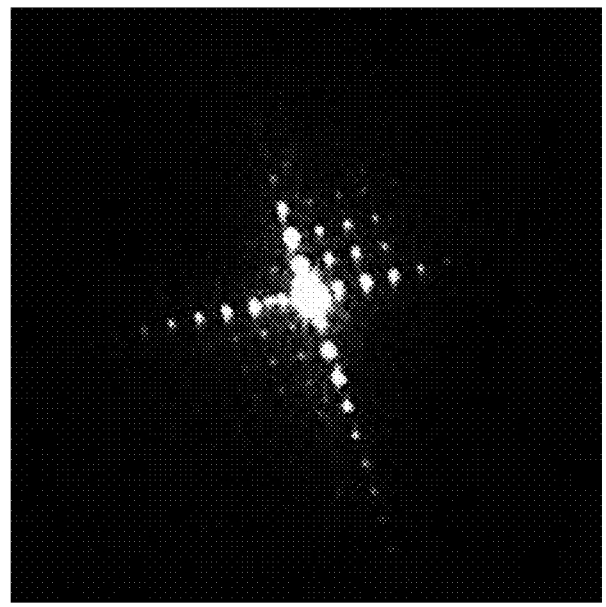
FIG. 3 is a small-angle electron beam scattering result obtained in transmission mode using a converging beam scheme to be discussed in one implementation of this invention. The test sample was a carbon film with a 473 nm×473 nm square pattern.

FIG. 3 is a CHD result of a 473 nm×473 nm square pattern imprinted on a carbon film using a TEM operated at 100 KeV. The corresponding value of $L_{\mathit{eff}}$ is near 80 m after being calibrated with the HD result from the identical sample. While keeping all the settings of the lenses fixed at the values led to FIG. 3 a copper line grating with a nominal 200 nm repeat on silicon wafer was loaded inside the TEM sample chamber. The line grating was oriented parallel to the incident electron beam and the sample surface was aligned to bisect the beam.

Figure 4:
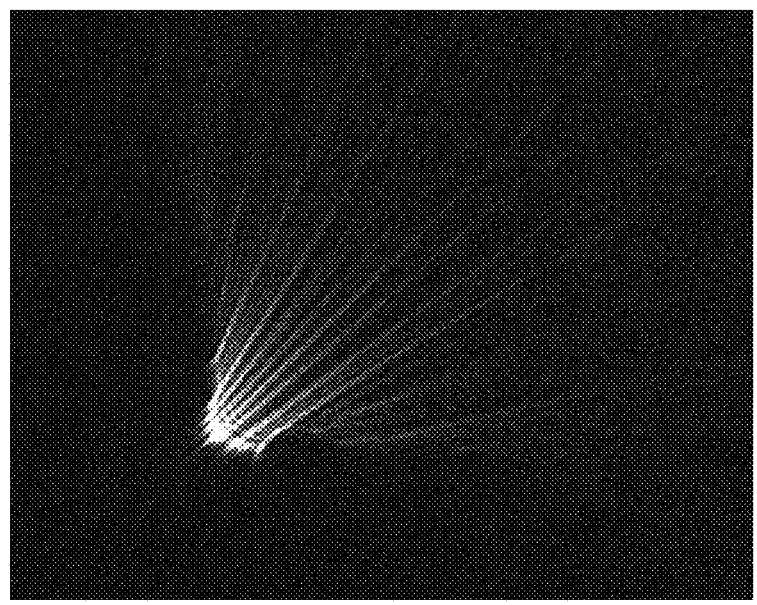
FIG. 4 is a small-angle electron beam scattering result obtained in reflection mode using a converging beam scheme to be discussed in one implementation of this invention.

By slightly tilting the incident beam towards the sample surface so that the incident beam illuminated the sample surface at a low grazing angle and the direct beam was completely blocked by the sample surface, the scattering pattern given in FIG. 4 was obtained. Many intricate features appear in this pattern and they are qualitatively different from the typical grazing incident small-angle X-ray scattering (GISAXS) pattern from similar line gratings. [J. Wernecke, M. Krumrey, A. Hoell, R. J. Kline, H. K. Liu and W. L. Wu, J. Applied Crystallography 47(6) (2014) pp. 1912-20]. This GISAXS data from line gratings have been quantitatively accounted for via the kinematical scattering process.

For the present case of the RSAES result given in FIG. 4, the kinematical scattering process is apparently inadequate and one has to resort to dynamic scattering theory, as with the cases of most electron scattering events. This observation indicates that the data interpretation of RSAES is not as straightforward as for GISAXS, nonetheless, the result, especially the fine fringes appearing along the sample shadow direction, adequately demonstrates that RSAES data can be acquired at a high resolution even using a TEM operated at 100 KeV which is far from the ideal voltage of low KeV for electron reflection measurements.

Figure 5:
FIG. 5 is an electron beam image in reflection mode obtained from the sampling area where the scattering result given in FIG. 4 was obtained.

To ensure that the RSAES result given in FIG. 4 is indeed from a reflection scattering geometry, the intermediate lenses, to a certain extent functioning as the electron projection optics (FIG. 1), were adjusted to return to the imaging mode from the RSAES settings; the result is given in FIG. 5. Note that the electron collimation optics as well as the sample position in terms of its displacements and angular alignments are all fixed throughout the above operation, i.e. the illumination condition of the sample was identical between FIG. 4 and FIG. 5.

Gratings are clearly visible in FIG. 5; a clear demonstration that the high resolution scattering pattern of FIG. 4 was from a grating area and was collected in a reflection mode. To enhance the image quality in acquiring FIG. 5, an objective aperture was inserted and was also visible in this figure. It is obvious that the amplitude of a Fourier transform of FIG. 5 will not lead to the pattern of FIG. 4, i.e. the dynamic scattering analysis including both elastic and inelastic events will be needed to extract quantitative information from RSAES data.

2. Small-Angle Electron Scattering in Backscattering Mode

Figure 6:
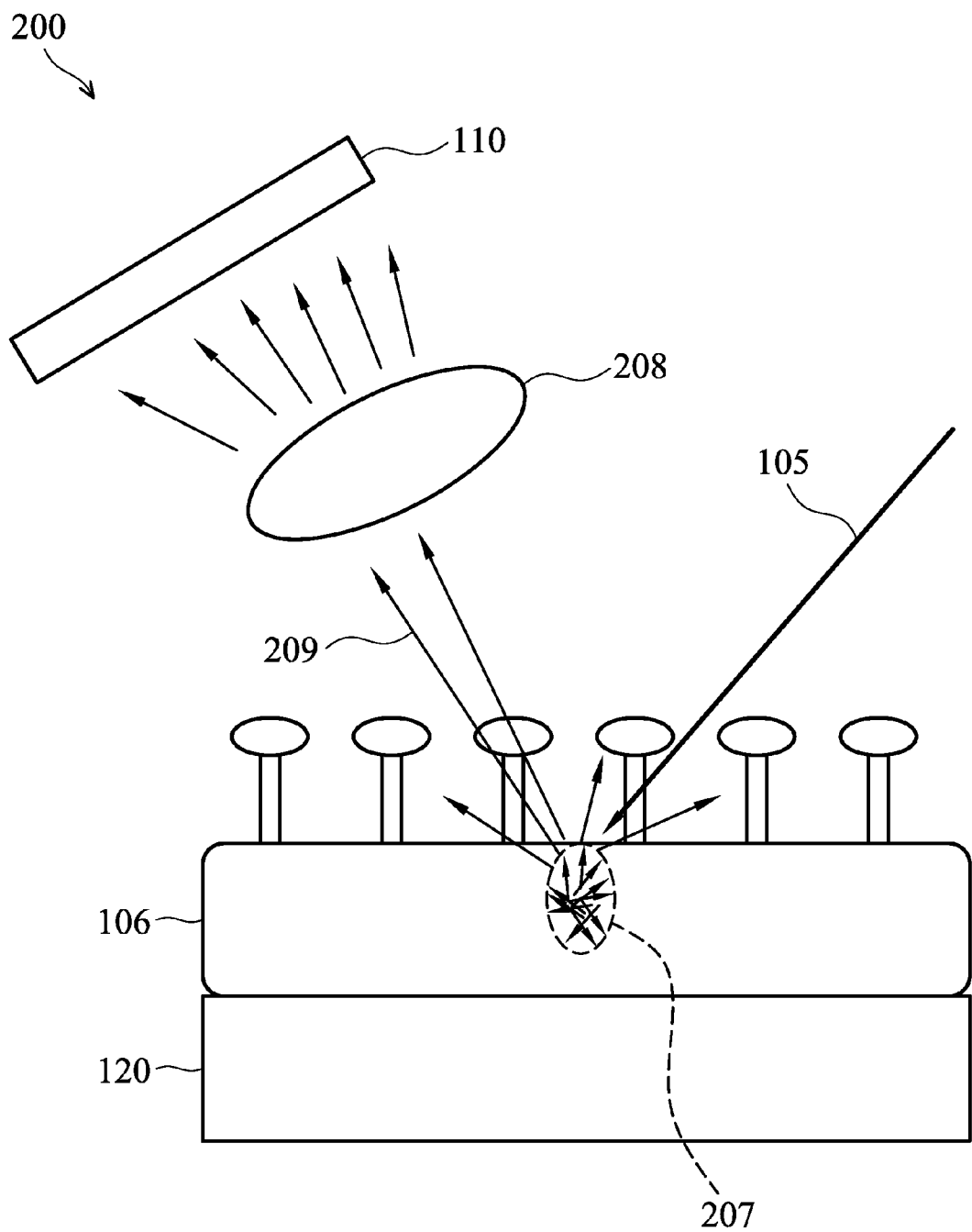
FIG. 6 is a schematic diagram of an electron beam small-angle backscattering measurement, in accordance with some embodiments.

FIG. 6 is the schematic diagram of a backscattering small-angle electron scattering (BSAES) apparatus 200 which shows another method to acquire information about the nanostructure on top of an opaque substrate. In FIG. 6, elements similar to those of the RSAES apparatus 100 are provided with the same reference numbers, and the features thereof are not repeated in the interest of brevity. For clarity, the electron collimation optics 104 and the electron source are not shown in FIG. 6.

The functions of all the components in system 200 are similar to those of system 100 except that a glazing angle magnifying component (e.g., electron beam deflectors/ prisms) may not be utilized in the electron projection optics 208 because the BSAES signals can be collected at a high take-off angle from the sampling area.

In accordance with some embodiments of the invention, the incident electron beam 105, after impinging the sample 106, results in a small excited volume 207 from which the backscattered electrons 209 emanate out in all directions. These backscattered electrons 209 are further scattered by the nanostructure to provide useful information. The backscattered electrons 209 originate from a small excited volume 207 within the sample 106 pass through the nanostructure and the electron projection optics 108 before being recorded by the electron detector module 110.

The abovementioned scattering process by the backscattered electrons is similar to a well-known art that led to Kikuchi patterns [S. Kikuchi, (1928a), Diffraction of cathode rays by mica. Proc. Imp. Acad. JPN 4, 271-4. (1928b), further study of the diffraction of cathode rays by mica. Proc. Imp. Acad. Jpn 4, 275-8] where the target is a crystalline lattice and the relevant length scale is the atomic distance of a few tenths of a nanometer. Unlike the previous case of SAES in reflection mode wherein a TEM can be modified to demonstrate certain aspects of its feasibility; for SAES in backscattering mode or BSAES, there is no commercial instrument available for demonstrating its feasibility.

This disclosure provides an apparatus, methods and a system of electron beam scattering for acquiring nanostructure information from samples on top of an opaque substrate. It requires minimum sample preparation and is noninvasive. Rather than focusing the electron beam onto a tiny spot on the sample, in one embodiment this invention is preferred to cover the entire sampling area with the electron beam. This enables the use of a high beam current while keeping the beam current density at a level consistent with the noninvasive requirement. As to the desirable incident beam cross section, let's look at the following example: for a sampling area of 0.1 mm×0.1 mm illuminated at a low grazing angle of one degree, the desired cross section of the incident beam immediately before the sample is a ribbon one instead of a square one. It can also be an elongated ellipse instead of a circular one. The aspect ratio of the ribbon or the ellipse depends on the incident angle as $1/\sin \theta_i$ where $\theta_i$ denotes the grazing incident angle.

The present invention is outlined in FIG. 1 and FIG. 6 which are not to scale; they are intended to be illustrative and not limiting to a particular implementation. In the above descriptions, numerous specific details are given to provide a thorough understanding of embodiments of the invention. However, the above descriptions of illustrative embodiments of the invention are not intended to be exhaustive or to limit the invention to the precise forms disclosed. One skilled in the relevant art will recognize that the invention which can be practiced without one or more of the specific details, or with other methods, components, etc. In other instances, well-known structures or operations are not shown or described in detail to avoid obscuring aspects of the invention.

What is claimed is:

1. A high angular resolution electron scattering apparatus for characterizing surface features in nanometers from a sample in either a reflection mode, or a backscattering mode or both, wherein the sample comprises an opaque substrate which is made of materials with a thickness that is impenetrable by electrons in KeV ranges, and the sample has a diameter of up to 40 cm or larger, the electron scattering apparatus comprising:
   a sample stage configured to hold the sample;
   an electron source configured to produce an electron beam;
   a plurality of electron collimation optics configured to receive the electron beam from the electron source and direct the electron beam to the sample stage;
   a plurality of electron projection optics; and
   an electron detector module, wherein the electron projection optics are configured to receive scattered/reflected electrons from the sample and direct the scattered electrons to the electron detector module, wherein a value of effective distance from the sample to the electron detector module is up to about 100 meters or more;
   wherein angular resolution is in a range from about $10^{-4}$ rad to about $10^{-5}$ rad, and the electron collimation optics and the electron projection optics are configured and operated in coordination to achieve the angular resolution.

2. The electron scattering apparatus as claimed in claim 1, wherein the combination of the electron source and the electron collimation optics is configured to enable the control of the grazing incident angle, the azimuthal angle, the position, the size and the cross section shape of the electron beam on the sample, wherein the size of the electron beam on the sample is from several micrometers to tens of micrometers in its linear dimension.

3. The electron scattering apparatus as claimed in claim 1, wherein the electron collimation optics and the sample stage are operated in coordination to direct the electron beam to different areas on the sample in scanning, non-scanning, step scanning, or continuous scanning modes.

4. The electron scattering apparatus as claimed in claim 1, wherein the electron collimation optics and the electron projection optics comprise components selected from the group consisting of electromagnetic lenses, magnetic lenses, electrostatic lenses, apertures, mirror, deflectors and prisms.

5. The electron scattering apparatus as claimed in claim 1, wherein the acceleration voltage of the electron beam is preferably in a range of about 20 KeV or less for operation in reflective mode, and the acceleration voltage of the electron beam can be higher than 20 KeV for operation in backscattering mode, wherein the convergence angle of the electron beam is either parallel, convergent or divergent.

6. The electron scattering apparatus as claimed in claim 1, wherein the electron source, the electron collimation optics, and the electron projection optics are configured to operate in tandem to achieve the desired angular resolution up to $10^{-5}$ rad.

7. The electron scattering apparatus as claimed in claim 1, further comprising an energy filtering member before or in the electron detector module to enable the selection of the range of the energy of the electron received by the electron detector module, wherein this range comprises that of the elastically scattered electrons to those of the inelastically scattered ones.

8. The electron scattering apparatus as claimed in claim 1, wherein the sample stage is capable of aligning the sample in its height and lateral position in nanometers and is capable of aligning the sample in all three Euler angles in mrad.

9. The electron scattering apparatus as claimed in claim 1, wherein the electron source and the electron collimation optics are configured and operated in coordination to enable a grazing incident angle of the electron beam from less than one degree to near 90 degrees.

10. The electron scattering apparatus as claimed in claim 1, wherein the electron projection optics and the electron detector module are configured and operated to receive electrons at low grazing exit angle of less than one degree to a high grazing exit angle near 90 degrees.

11. The electron scattering apparatus as claimed in claim 1, wherein the electron detector module comprises multiple detectors of various types and configured to receive many types of signals resulting from the interactions between the electron beam and the sample,
   wherein the signals comprise scattered electron, reflected electron, secondary electron, Auger electron, and fluorescent X-ray, thereby the electron detector module produces complementary information comprising sample composition, film thickness and chemical bonds, surface charge distribution and local electric conductivity.

12. The electron scattering apparatus as claimed in claim 1, wherein the electron projection optics and the electron detector module are configured and operated to receive electrons from the diffraction of certain crystalline parts of the nanostructures.

13. The electron scattering apparatus as claimed in claim 1, wherein the electron projection optics and the electron detector module are configured and operated to detect diffracted electrons and the surrounding scattered electrons with an angular resolution up to $10^{-5}$ rad.

14. The electron scattering apparatus as claimed in claim 1, wherein the electron source, the collimation optics and the sample stage are configured and operated to reach a surface wave resonance diffraction condition to enhance the intensity of the diffracted electrons of interests.

15. A high angular resolution electron scattering method for characterizing surface features in nanometers from a sample in either a reflection mode, or a backscattering mode or both, wherein the substrate comprises an opaque substrate which is made of materials with a thickness that is impenetrable by electrons in KeV ranges, and the sample has a diameter of up to 40 cm or larger, the method comprising:

holding the sample by a sample stage which allows for a positioning of the sample in all three directions and all three Euler angles;
   producing an electron beam;
   directing the electron beam to a sampling area of the sample by electron collimation optics;
   receiving the scattered electrons from the sample and magnifying their angular distribution by electron projection optics, and angular resolution is in a range from about $10^{-4}$ rad to about $10^{-5}$ rad;
   collecting the scattered electrons by an electron detector module, wherein a value of effective distance from the sample to the detector module is up to about 100 meters or more; and
   outputting a data array with the angular information encoded in the position of the array, and/or outputting a data array which has been energy resolved in each data point of the array via an energy filter incorporated in the electron projection optics or via a detector with an energy resolving capacity at each pixel.

16. The method as claimed in claim 15, wherein the scattered electrons are detected by multiple detectors of various types, the detectors are configured to receive many types of signals resulting from the interactions between the electron beam and the nanostructures within the sampling area,
   wherein the signals comprise scattered electron, reflected electron, secondary electron, Auger electron, and fluorescent X-ray, thereby the detectors provide complementary information comprising sample composition, film thickness and chemical bonds, local electric conductivity and surface charge distribution.

17. The method as claimed in claim 15, wherein the electron detector module, the electron projection optics and the sample stage are configured and operated to align, to receive and to magnify any specific diffraction electrons and the surrounding scattered electrons.

18. The method as claimed in claim 15, wherein the electron detector module, the electron projection optics, and the sample stage are configured and operated to reach a surface wave resonance diffraction condition to enhance the intensity of the diffraction beam of choice.

19. The method as claimed in claim 15, wherein voltage distributions or sample charges across various nanostructures in the sampling area are appraised, while the voltage or charges can be resulted from the impinging electron beam, applied voltage on the sample, the difference in the local electric conductivity, and the mean internal potential of electron among materials and others.

20. The method as claimed in claim 15 used together with other techniques including and not limited to scanning electron microscopy and optical scatterometry to provide information about the sampling area, wherein the information comprises critical dimensions, shapes, composition distributions, and defects in the nanostructures in the sampling area.

21. A high angular resolution electron scattering system for characterizing surface features in nanometers from a sample in either a reflection mode, or a backscattering mode or both, wherein the substrate comprises an opaque substrate which is made of materials with a thickness that is impenetrable by electrons in KeV ranges, and the sample has a diameter of up to 40 cm or larger, the electron scattering apparatus comprising:

means to generate an electron beam;
   means to receive, to collimate and to direct the electron beam to a sampling area on the sample;
   means to hold the sample and to allow for a precise positioning of the sample in all three directions and all three Euler angles;
   means to receive and to magnify scattered electrons from the sample;
   means to collect the electrons from the electron projection optics and to output a two dimensional data array with the angular information encoded in the position of the array; and
   means to collect the electrons from the electron projection optics and to output a two dimensional data array with the data which has been resolved in each point of the data array,
   wherein a value of effective distance from the sample to a position where the electron is collected is up to about 100 meters or more.

* * * * *